United States Patent [19]
Gualy et al.

[11] Patent Number: 5,492,603
[45] Date of Patent: Feb. 20, 1996

[54] APPARATUS FOR RECOVERING ACETIC ACID FROM AQUEOUS STREAMS

[75] Inventors: Ronald G. Gualy, Arlington, Tex.; Wiston Lamshing, Cosoleacaque, Mexico; Joseph C. Gentry, Dallas, Tex.; Fernando Varela, Minatitlán, Mexico

[73] Assignee: Glitsch, Inc., Dallas, Tex.

[21] Appl. No.: 187,084

[22] Filed: Mar. 15, 1994

Related U.S. Application Data

[62] Division of Ser. No. 90,765, Jul. 12, 1993, Pat. No. 5,409,579.

[51] Int. Cl.$^6$ ............................... B01D 3/16; B01D 11/04
[52] U.S. Cl. ..................... 202/158; 202/169; 202/183; 203/16; 203/87; 203/DIG. 6
[58] Field of Search ..................... 203/16, 46, 42, 203/87, DIG. 9, DIG. 6; 202/168, 169, 170, 158, 183, 184; 562/608, 513

[56] References Cited

U.S. PATENT DOCUMENTS

| | | | |
|---|---|---|---|
| 998,234 | 7/1911 | Crossley et al. | 203/42 |
| 2,269,163 | 1/1942 | Othmer | 203/16 |
| 2,333,756 | 11/1943 | Wentworth | 203/16 |
| 2,588,268 | 3/1952 | Mercer et al. | 203/16 |
| 2,684,934 | 7/1954 | Weaver et al. | 203/46 |
| 2,690,995 | 10/1954 | Steitz | 203/46 |
| 4,143,066 | 3/1979 | Kalcevic | 203/16 |
| 4,230,887 | 10/1980 | Mitchell et al. | 203/16 |
| 4,769,487 | 9/1988 | Hundley et al. | |
| 5,057,192 | 10/1991 | Zoeller et al. | 203/46 |
| 5,078,900 | 1/1992 | Wegner . | |
| 5,175,357 | 12/1992 | Van Brunt . | |

FOREIGN PATENT DOCUMENTS

| | | |
|---|---|---|
| 1113957 | 12/1981 | Canada . |
| 53-71034 | 6/1978 | Japan . |
| 53-79836 | 7/1978 | Japan . |
| 56-4587 | 1/1981 | Japan . |
| 58-39812 | 3/1983 | Japan . |
| 59-33579 | 2/1984 | Japan . |
| 1583755 | 2/1981 | United Kingdom . |

*Primary Examiner*—Wilbur Bascomb, Jr.
*Attorney, Agent, or Firm*—Jenkens & Gilchrist

[57] ABSTRACT

Disclosed is a method and apparatus for recovering acetic acid from an acetic acid/water waste stream which includes a dehydration column into which the stream is fed and a liquid-liquid extraction system for recovering acetic acid from the condensate of the overhead stream of the dehydration column. Optionally, low pressure and/or high pressure absorber systems are provided to process vapor and/or liquid streams associated with the recovery system and/or the plant in which the acetic acid is used to further the recovery of acetic acid and reduce atmospheric pollution.

18 Claims, 8 Drawing Sheets

FIG. 1 (PRIOR ART)

EXTRACTION SYSTEM WITH HEAVY BOILER SOLV.

FIG. 2A

FIG. 4 (EXTRACTION SYSTEM)

*FIG. 5*

*FIG. 6*
(EXTRACTION SYSTEM)

FIG. 7 (EXTRACTION SYSTEM)

FIG. 8 (EXTRACTION SYSTEM)

FIG. 9 (EXTRACTION SYSTEM)

FIG. 10 (EXTRACTION SYSTEM)

APPARATUS FOR RECOVERING ACETIC ACID FROM AQUEOUS STREAMS

This application is a division of application Ser. No. 08/090,765, filed Jul. 12, 1993 now U.S. Pat. No. 5,409,579.

This invention relates to a new method and apparatus for recovering acetic acid, which is the solvent typically used in the production of terephthalic acid and is also a recoverable waste stream in other important industrial processes. The method and apparatus provide a significant reduction of energy consumption, allow an increase in capacity for existing plants, and eliminate the organics emission problem currently existing in most terephthalic acid production plants.

In a preferred form, the invention provides a modification to existing acetic acid distillation systems in conjunction with a new extraction system for acetic acid and a new absorption method.

BACKGROUND OF THE INVENTION

Acetic acid is a recoverable solvent utilized in the production of terephthalic acid in many processes. See U.S. Pat. No. 4,769,487, British 1,583,755, Canadian 1,113,957, and Japanese 53-71034, 58-39812, 59-33579, 53-79836, and 56-4587.

Distillation has been widely used as a primary unit operation for acetic acid recovery in such processes, utilizing one or more towers to process a number of streams of varying concentrations of acetic acid with the purpose of recovering it for further use in the oxidation step. The products from the distillation tower are a bottom stream of concentrated acetic acid, and an overhead stream that ideally would be pure water.

Because of the high non-ideality of the system acetic acid/water and the equilibrium limitation in such a system, it is necessary to utilize a distillation tower with a high number of theoretical stages and high reflux ratio to be able to obtain reasonably low levels of acetic acid in the distilled water.

These involve a high investment cost because of the large dimensions of the required equipment and a high operating cost because of the high steam consumption involved. Furthermore, the traditional process scheme does not allow one to obtain economically a distillate completely free of acetic acid. This limitation, in turn, presents two main problems: a cost associated with the operation resulting from the acetic acid losses, and an environmental problem that is continually increasing, because of the ever more rigorous standards for acceptable levels of emission to the environment.

There has been an effort to look for alternatives to solve the problem. Resort has been had to azeotropic distillation, involving the addition of an additional component to the distillation tower to improve the relative volatility of the separation and reduce the separation requirements. This existing option provides some reduction in the operating costs, but it generates some additional operating and environmental problems.

A study of the vapor liquid equilibrium of the components acetic acid/water shows the difficulty in the dilute acetic region of reducing the acetic acid in the distilled water. The achievement of a reduction from the typical design value of 0.5 wt % acetic acid overhead to 0.1 wt % acetic acid overhead requires an increase in reflux ratio of about 10–15% or the inclusion of several additional theoretical stages to maintain the same reflux ratio.

Extraction of Acetic Acid in Dilute Streams

For several years it has been known that the use of liquid-liquid extraction is a way to recover acetic acid from dilute streams. Several extractive agents have been identified, and it is possible to economically recover acetic acid from streams containing 0.1 wt % acetic acid to 20% acetic acid. Some of the agents usually used are acetates, amines, ketones and phosphine oxides and mixtures thereof.

Once the extraction step is completed, a series of distillation steps are required to recover the acid and to recirculate the extractive agent back to the extraction stage. The level of impurities in the feed and the affinity of the particular extractive agent for water dictate the additional steps required in the system.

SUMMARY OF THE INVENTION

The present invention is based on the specific application of known unit operations technologies and careful selection of recently developed extractive agents for acetic acid that independently of each other do not produce the major advantages seen in the invention, but when these approaches are exploited together in the present arrangement, they provide a new process scheme with the benefits previously discussed.

A significant reduction of energy required (as measured by reflux ratio) can be obtained by relaxing the specification for the acetic acid overhead composition in the acetic acid recovery still from 0.1 wt % acetic acid to 0.5 wt % acetic acid which can result in a 10–15% reduction in energy consumption. A further relaxation of the overhead acetic acid composition requirement from 0.5 wt % acetic acid to 10% acetic acid can result in a 40–50% reduction in energy consumption.

In accordance with the invention, a higher concentration of acetic acid in the overhead stream is accepted. Thus the reflux ratio is reduced, and the internal loadings of a typical acetic acid dehydration tower are reduced, representing a considerable increase in capacity. Further in accordance with the invention, a new system is provided to handle the additional acid in the overhead. In a preferred form of the invention, an extraction unit is provided to handle the overhead stream of the dehydration tower.

The extraction unit is capable of handling from 2% to 20% acetic acid in the overhead stream and may use any of the known extraction solvents (ethyl acetate, other acetates, primary amines, secondary amines, ternary amines, MEK MiBK, other ketones, phosphine oxides). The preferred solvents are the phosphine oxides commercialized by Cytek (formerly American Cyanamid) under the Cyanex name, and amines. Since the operating requirements of the acetic acid dehydration column have been changed drastically, it is also possible to change the typical flowsheet of the plant. With the system of the invention, diluted acid streams (0.5 wt %–40 wt %) previously sent to the dehydration column may now be fed directly to the extraction system. This represents a large energy savings for the overall solvent recovery system, because the water in these streams need not be evaporated, and it will give an additional capacity increase for the dehydration column.

To increase capacity in a limited dehydration column, a new column is typically needed. For a 300,000 MTY plant, the investment in a new column for a 30% increase capacity can be between 6–8 million dollars. The system of the invention may be built for about half of that amount and achieve not only the capacity increase, but also reduction of emissions to the atmosphere.

Another major aspect of the present invention scheme is the inclusion of new high pressure and low pressure absorption systems in the recovery system. In current designs of typical terephthalic acid production plants, $N_2$ is introduced to the dehydration system. This creates a stream of non-condensables that entrains acetic acid, and some acetic acid is eventually carried to the atmosphere. In addition, the typical design presents a vent in the overhead vapor line that continuously sends organics to the atmosphere.

In the invention, two ways to improve and reduce these emissions of organics are provided. A preferred arrangement is to use the liberated condensing capacity in the dehydration column to condense more of the organics in conjunction with a new low pressure absorber system to remove the acids that are still not condensed. The new low pressure absorber system can handle all the low pressure vents from the plant and primarily the vent from the overhead vapor line and the overhead condenser vent line. The absorption liquid may be chilled water, diluted acetic acid (from a stream previously sent to dehydration) or preferably, a phosphine oxide solvent (Cyanex). In the case of using chilled water or diluted acetic acid, the bottom stream from the low pressure absorber may be sent to the new extraction unit. In the case of using the phosphine oxide, the stream is sent to the recovery tower of the extraction system.

Currently in a typical production plant design there are two high pressure absorbers used to recover organics from the oxidizer overheads. The first uses acetic acid primarily to recover p-xylene and methyl acetate; and the second uses water from the overheads of the dehydration column to recover the remaining acetic acid. In the invention scheme, both high pressure absorbers may be combined into one, if desired, or the second absorber may be changed to use phosphine oxide as the absorption solvent. This change eliminates a water recirculation stream in the plant from the high pressure absorber to the dehydration tower and back to the high pressure absorber. The benefits are an improvement in energy efficiency and capacity in the recovery system. The phosphine oxide stream from the one absorber or the secondary absorber reduces the emissions from the oxidizer overheads by improving absorption.

The combination of the high pressure absorber modification and the new low pressure absorber system helps terephthalic acid production plants to economically reduce atmospheric emission levels to values lower than those required by environmental agencies.

Another area where the invention presents great benefits for the typical production plant is in the water handling. At present the water stream most typically discharged to neutralization is the overhead of the dehydration column with acetic acid values between 0.2 wt % to 1 wt %. This represents a heavy and objectionable lead on the neutralization/biological treatment section of the plant. The arrangement of the invention provides a significant reduction of acetic acid in the water levels to about 100 ppm to 500 ppm by weight, dependent on the plant requirements. (The expected solvent content is between 10 ppm wt. to 200 ppm wt.) Such water with this concentration can be used as cooling water or process water in the plant after a suitable treatment with activated carbon. Another major use of this water, for the case where the acetic acid content is low, can be as a solvent for the crystallization of terephthalic acid. This provides a considerable reduction of water usage in the plant by using the water produced in the oxidation step of terephthalic acid production for most of the plant needs.

In general, by including all aspects of the invention in the process by specific uses of known technologies, a greatly improved process for recovering the solvent in the production of terephthalic acid is achieved. The new process generates benefits of increased capacity, reduction of energy consumption and a great reduction in organic emissions to the atmosphere as well as to the treatment plant.

In accordance with a preferred embodiment of the invention, there is provided an acetic acid and water separation system for use in a plant utilizing a water solution of acetic acid, which system includes a dehydration device, which is preferably and most usually a column that is equipped to receive at least one input acetic acid-containing water stream from said plant and to apply heat to said input stream received by said column to separate acetic acid from water in the column to thereby produce an output bottom stream of relatively concentrated acetic acid in water, and an output overhead stream of relatively dilute acetic acid in water. Also included are condensing means to liquify acetic acid and water from said output overhead stream to form an output overhead condensate. The system is also provided with a liquid-liquid extraction system that has a contactor to receive said output overhead condensate and contact it with a liquid extractant to extract acetic acid from said condensate and thereby form a first contactor output stream containing acetic acid and extractant, and a second contactor output stream containing water, and also has an extraction system separator column equipped to receive said first contactor output stream and separate the acetic acid and the extractant therein to produce an extractant output stream for recycle to said contactor and an acetic acid output stream.

When the acetic acid and water separation system just described employs a liquid extractant which boils at a temperature higher than acetic acid, the acetic acid output stream from said extraction system separator column is an overhead stream therefrom, while on the other hand, when a liquid extractant which boils at a temperature lower than acetic acid is used, the acetic acid output stream from said extraction system separator column is a bottoms stream therefrom.

The acetic acid and water separation system described above may include means for feeding at least one additional relatively dilute acetic acid stream from said plant to its liquid-liquid extraction system along with the output overhead condensate stream from the dehydration column, and this stream may be a bottoms stream from a high pressure absorber in said plant, or a condensate stream from a drying system.

The acetic acid and water separator system described above may also include a low pressure absorption unit adapted to contact an absorption solvent with at least one acetic acid containing vapor stream from said acetic acid and water separation system, and further adapted to feed absorption solvent after contact with said vapor stream to said liquid-liquid extraction system. The acetic acid containing vapor stream may be at least a portion of the output overhead stream from said dehydration column, or a portion of a vent stream from an output overhead condenser adapted to process the output overhead stream from said dehydration column, or may be an acetic acid containing vapor stream from a point in said plant other than said acetic acid and water separation system. Furthermore, the acetic acid and water separation system described above may also include means for feeding at least one additional relatively dilute acetic acid stream from said plant to said liquid-liquid extraction system along with said output overhead stream from said dehydration column. The additional relatively dilute acetic acid stream may be a bottoms stream from a high pressure absorber in said plant, or a condensate stream from a drying system. The acetic acid and water separator system first described above may further comprise a high pressure absorber system equipped to contact an absorbent liquid at high pressure with a plant overhead vapor stream having acetic acid therein, and means for delivering said absorbent liquid, after contact with said plant overhead vapor stream to said separator system for processing therein. Said delivering means may be connected to deliver said absorbent liquid to said dehydration column or may be connected to deliver said absorbent liquid to the contactor of said liquid-liquid extraction system. Alternately, said delivering means may be connected to deliver said absorbent liquid to the extraction system separator column of said liquid-liquid extraction system.

DETAILED DESCRIPTION OF PREFERRED EMBODIMENTS

Figure 1:
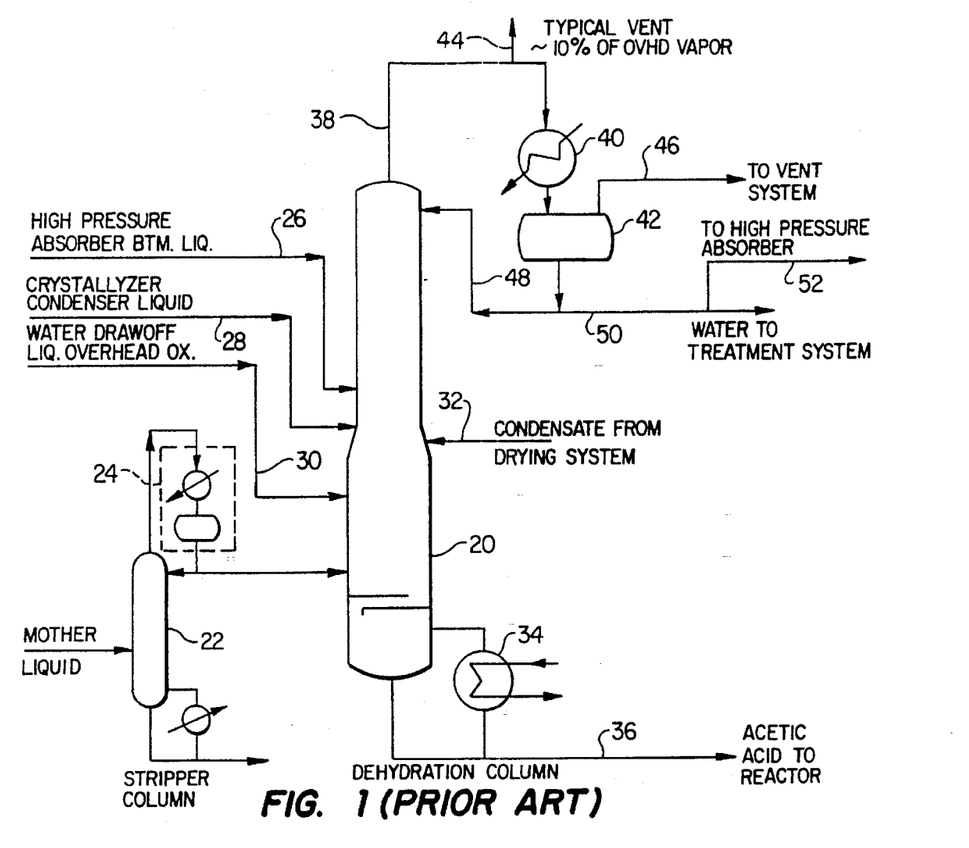
FIG. 1 is a flow diagram of an acetic acid recovery system as typically found in the prior art.

FIG. 1 illustrates a flow diagram of a typical prior art acetic acid recovery system. The primary unit in the recovery system is a dehydration column 20. The column 20 receives input from several sources, one being the overhead from a stripper column 22, which in turn is fed mother liquor from the plant. The bottom stream from stripper column 22 is rich in acetic acid and is returned to the plant for reuse. The stripper column 22 has an optional condenser system 24.

Other feed input streams to the dehydration column 20 include line 26, which delivers bottom liquid from a high pressure absorber in the plant, line 28, which delivers liquid from a crystallizer, and line 30, which delivers water draw off liquid from the overhead stream out of an oxidation unit, such as is found in a typical terephthalic acid synthesis plant. Line 32 also delivers to the dehydration column 20 condensate from a drying system within the plant. The dehydration column 20 may be packed with structured or random packing or equipped with trays of various styles. Heat is supplied to the dehydration column 20 through reboiler 34 and the bottom stream out of the column is rich in acetic acid which is returned to the plant for reuse through line 36.

The overhead line 38 from the dehydration column 20 leads to a condenser 40 and a separation drum 42. The overhead line 38 may be equipped with a vent 44. The separation drum 42 may include a vent 46. The bottom stream from drum 42 is split into a reflux line 48, and an overhead product line 50, which is primarily water for delivery to the waste water treatment system. Line 50 may have a branch carrying a portion, or even all, of the water stream, which is not returned as reflux through line 48, to a high pressure absorber for further recovery of acetic acid. The line to the high pressure absorber is line 52.

Figure 2A:
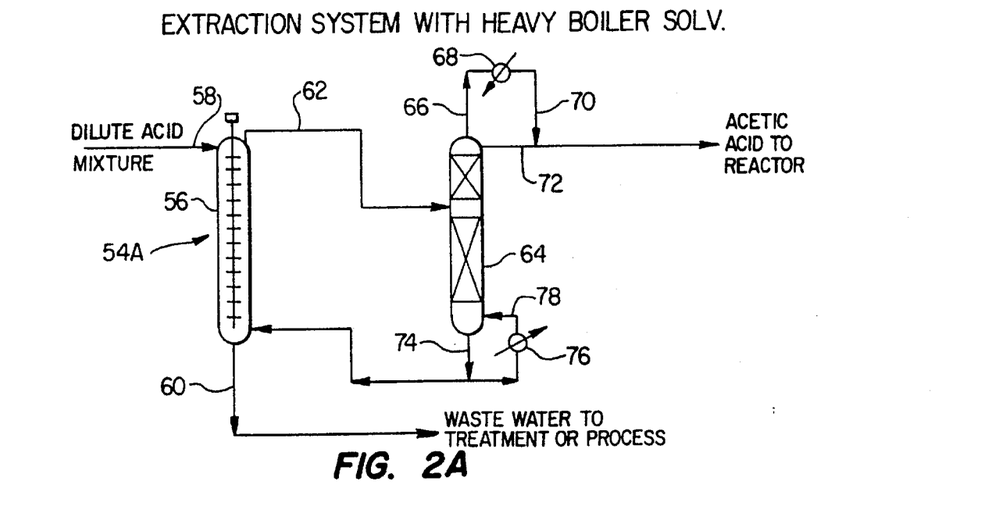
FIG. 2A is a flow diagram for an extraction system using an extractive solvent boiling at relatively high temperature.
Figure 2B:
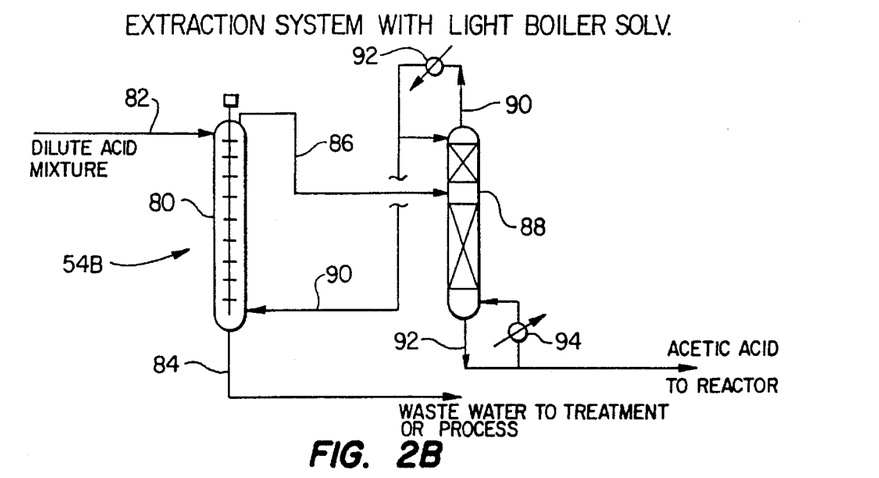
FIG. 2B is a flow diagram for an extraction system utilizing an extractive solvent which is relatively low temperature in boiling point.

Attention is now directed to FIGS. 2A and 2B, which illustrate extraction systems which may be employed in accordance with the invention. The extraction system of FIG. 2A is designed and adapted for use with an extraction solvent which is a "heavy boiler," that is, a solvent which boils at a temperature higher than the boiling point of acetic acid. This extraction system is designated generally 54A. The extraction system of FIG. 2B is one designed and equipped to utilize an extraction solvent which is a "light boiler," that is, one which boils at a lower temperature than acetic acid. In FIG. 2A, the extractor is designated 56, and receives dilute acetic acid through line 58 near its top. A bottom line 60 carries waste water to the waste water treatment plant or back into the terephthalic acid plant for reuse there. The overhead stream from the liquid-liquid contactor 56 is carried through line 62 to separator tower 64. The top stream out of separator tower 64 is carried by line 66 through condenser 68 and line 70 back to the plant for reuse. This stream is relatively highly concentrated acetic acid. If desired, a reflux may be provided through line 72. The bottom stream out of separator tower 64 is carried through line 74 back to the liquid-liquid contact device 56. A portion of the bottom stream may be carried through a reboiler 76 and returned through line 78 to the separator tower near its bottom. A heat exchanging device may be used to exchange heat between streams 62 and 74 for improved operation.

In FIG. 2B, the liquid-liquid extractor column is designated 80. It receives a dilute acetic acid feed through line 82. A bottom stream that is relatively pure water leaves the extractor through line 84 and is delivered to the treatment system for waste water or returned to the terephthalic acid plant for reuse there. The top stream consisting primarily of extraction solvent with acetic acid dissolved therein leaves the top of the liquid-liquid extractor 80 through line 86, which delivers it to separator column 88. The overhead line out of separator column 88 is designated 90, and this stream is relatively pure extraction solvent. A condenser 92 is preferably provided in line 90, which delivers the extraction solvent to a point near the bottom of extractor column 80. In separator column 88, the bottom stream is relatively concentrated acetic acid, which leaves through line 92; a reboiler 94 may heat part of this stream for return to the separator column 88 near its bottom. The bulk of the acetic acid in the bottom stream 92 is returned to the terephthalic acid plant for reuse there.

Figure 3:
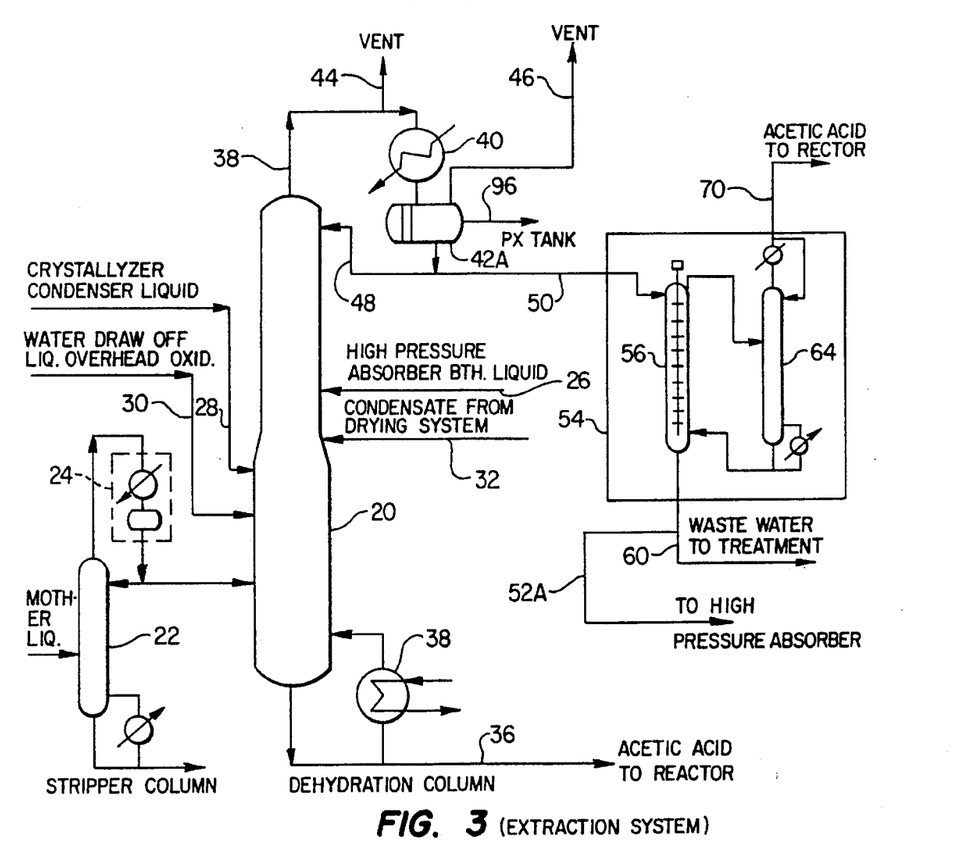
FIG. 3 is a flow diagram of an acetic acid recovery system constructed in accordance with the invention, in which an extraction system is equipped to receive and process condensate from the overhead stream of the dehydration column of the system.

FIG. 3 illustrates a preferred embodiment of the invention. In FIG. 3, as well as in FIGS. 4 and 6–10, which show other preferred embodiments of the invention, the items of equipment and lines which are substantially the same as the equipment pieces and lines shown in FIG. 1 are given the same reference number. When lines or equipment are illustrated in these figures which are similar, but differ in some respects either by structure or function, a letter designator such as "A" or "B" may be used in addition to the numerical designator. In the embodiment of FIG. 3, a single distillation column is shown for the primary dehydration step. Those skilled in the art will understand one or more such columns may be used, singularly or stagewise to separate the acids and entrained water from the solvent, and that other kinds of separation equipment may be included.

In FIG. 3, the acetic acid recovery system includes substantially all of the equipment provided in the prior art unit of FIG. 1 but, in addition, includes an extraction system designated 54. The extraction system may be either like the extraction system 54A of FIG. 2A or the extraction system 54B of FIG. 2B, depending upon the characteristics of the extraction solvent chosen for use in a particular plant. The extraction system 54 is constructed and arranged to receive input to the liquid-liquid extractor through line 50. The extraction unit 54 illustrated in FIG. 3 (and subsequent figures) is one designed for use with a heavy boiling extraction solvent, and is therefore drawn to conform with the extraction system shown in FIG. 2A. For this reason, its extractor unit is designated 56 and the separator is designated 64. The bottom stream out of liquid-liquid extractor 56 is a waste water stream 60 delivered to waste water treatment or, if desired, returned to the terephthalic acid plant for reuse. Furthermore, in accordance with this and succeeding embodiments of the invention, waste water from the extractor 56 may be delivered through line 52A to a high pressure absorber for use therein. The overhead stream out of separator 64 through line 70 is relatively concentrated acetic acid, which is returned to the reactor of the acid plant for reuse. The separator drum 42A in the overhead system from dehydration column 20 may include a coalescing device for separating paraxylene from both the overhead and bottom streams out of the drum, in which case a paraxylene withdrawal line 96 leading to a paraxylene accumulation tank is provided.

A comparison of the prior art plant of FIG. 1 with the acetic acid recovery system of the invention shown in FIG. 3 reveals that the primary difference is the provision of the extraction system 54 in the unit of the invention. This difference, while it appears to be simple, provides material advantages, because a high acetic acid concentration may be tolerated in the overhead stream from the dehydration column, thus lessening the energy demands of that column, without sacrificing the overall acetic acid recovery level, because the acetic acid in the dehydration column overhead stream is substantially all eventually recovered in the extraction system 54, at a much lower energy cost.

Figure 4:
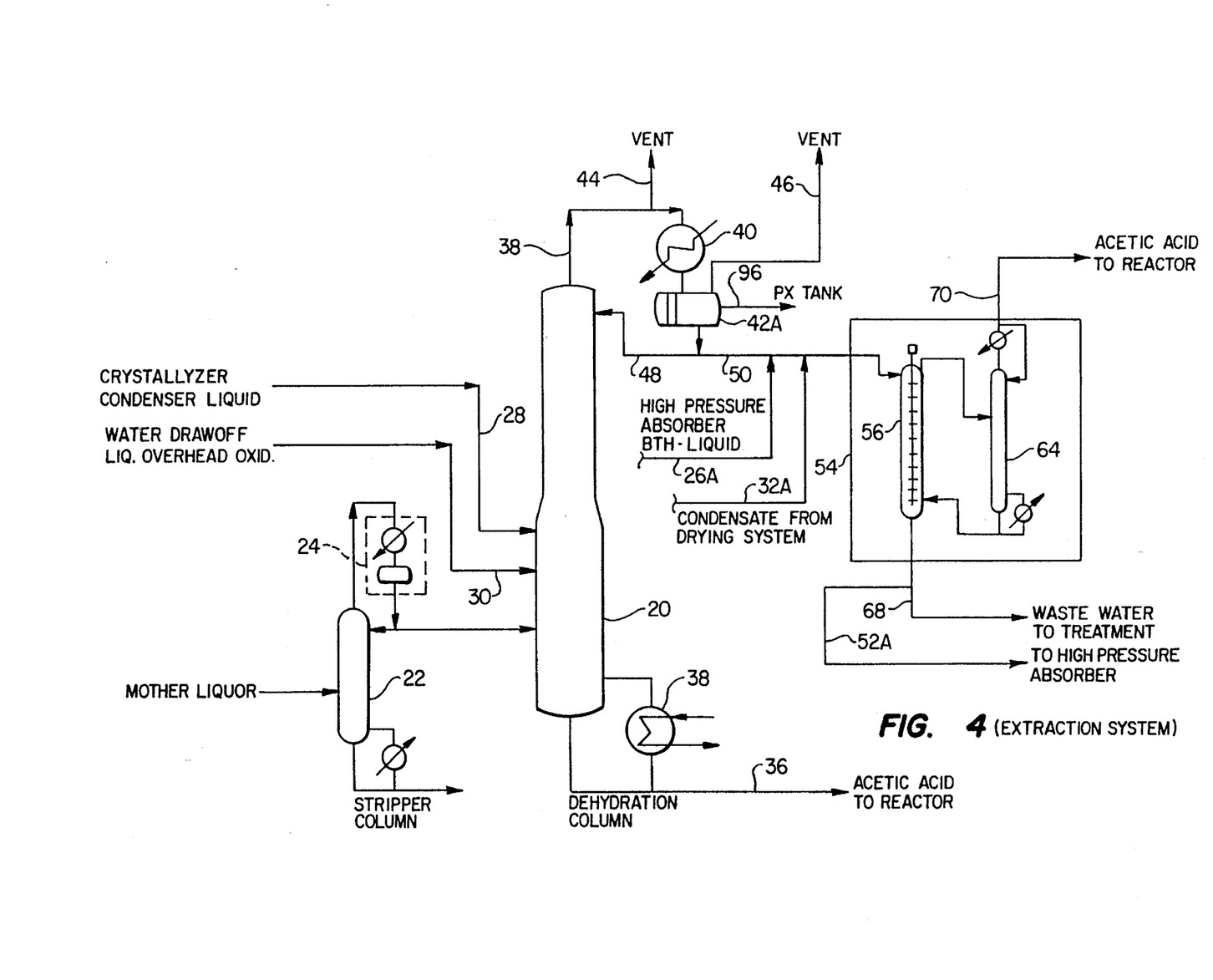
FIG. 4 is a flow diagram of an embodiment of the invention similar to that of FIG. 3, but in which relatively dilute acetic acid streams from plant locations are fed directly to the extraction system, rather than being fed to the dehydration column.

Attention is now directed to FIG. 4 which shows a further embodiment of the invention. The system of FIG. 4 is also provided with an extraction system 54 for processing overhead condensate delivered from the dehydration column. This embodiment differs from the embodiment of FIG. 3 in that high pressure absorber bottom liquid is delivered through line 26A directly to the extraction system in FIG. 4 instead of being delivered to the dehydration column through line 26 as is the case in FIG. 3. In addition, condensate from a drying system within the terephthalic acid plant is delivered through line 32A to the extraction system 54, instead of being fed to the dehydration column 20 through line 32 as is the case in FIG. 3.

This modification also represents an improvement, because the high pressure absorber bottom liquid and condensate from the plant drying system both contain a significant concentration of water which, in the embodiment of FIG. 3, is evaporated in the dehydration column. This energy intensive step is circumvented in the embodiment of FIG. 4, since these streams are fed directly to the liquid-liquid extraction column 56 in the extraction system 54.

Figure 5:
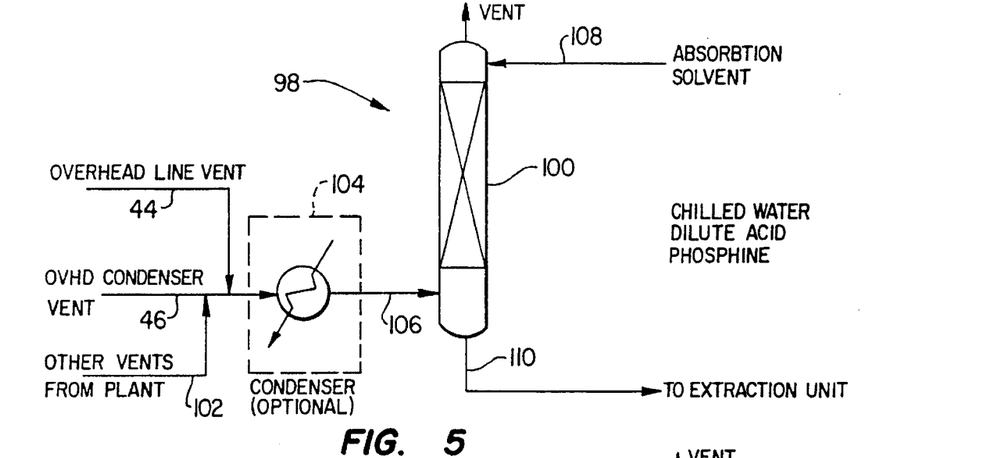
FIG. 5 is a flow diagram of a low pressure absorption unit which may be employed in accordance with certain embodiments of the invention.

FIG. 5 illustrates a flow diagram for a low pressure absorption unit useful in connection with the invention. The low pressure absorption unit of FIG. 5 is designated generally 98, and it includes an absorption tower 100, input for which may be drawn from several sources. These may include an overhead line vents from the dehydration column 44, a vent line from the condenser drum 42 or 42A designated 46, and other vents from the plant designated 102. Some or all of these may be fed through an optional condenser system 104 before being delivered to the absorption column 100 through line 106. Absorption solvent is fed to the absorption column through line 108, and the absorption solvent, now rich in acetic acid, leaves as a bottom stream 110 for delivery to an extraction unit of the kind illustrated in FIGS. 2A and 2B.

Figure 6:
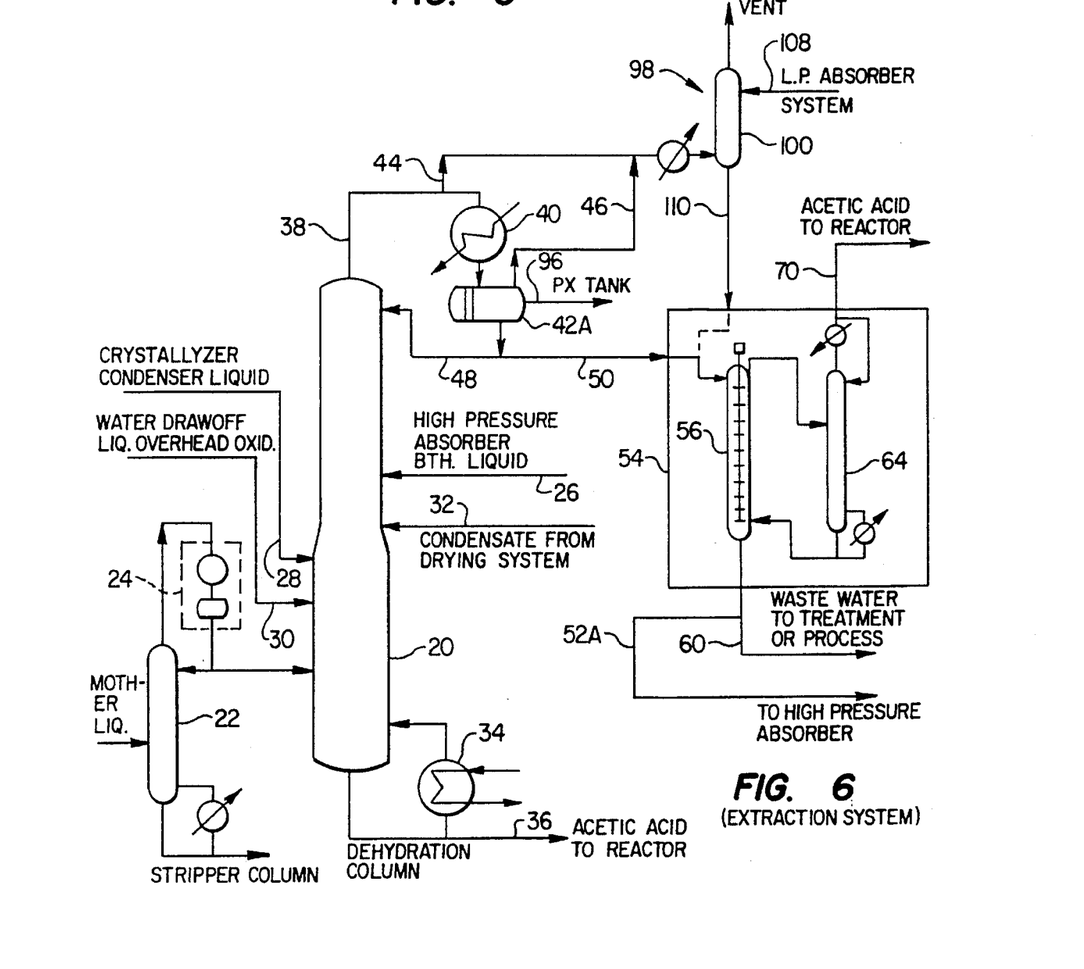
FIG. 6 is a flow diagram of an acetic acid recovery system in accordance with the invention in which the low pressure absorber system of FIG. 5 is employed in connection with the basic system as illustrated in FIG. 3, for example.

These arrangements are illustrated in the context of an overall system flow sheet in FIG. 6 where the low pressure absorption system is designated 98 and the absorption column is designated 100. As can there be seen, bottom line 110 delivers a stream relatively rich in acetic acid to the liquid-liquid extraction system 54, and in particular to the extraction column thereof 56. The embodiment of the invention illustrated in FIG. 6 is like that shown in FIG. 3, in that high pressure absorber bottom liquid is fed to the dehydration column 20 through line 26 and condensate from a plant drying system is also fed to that dehydration column through line 32.

Figure 7:
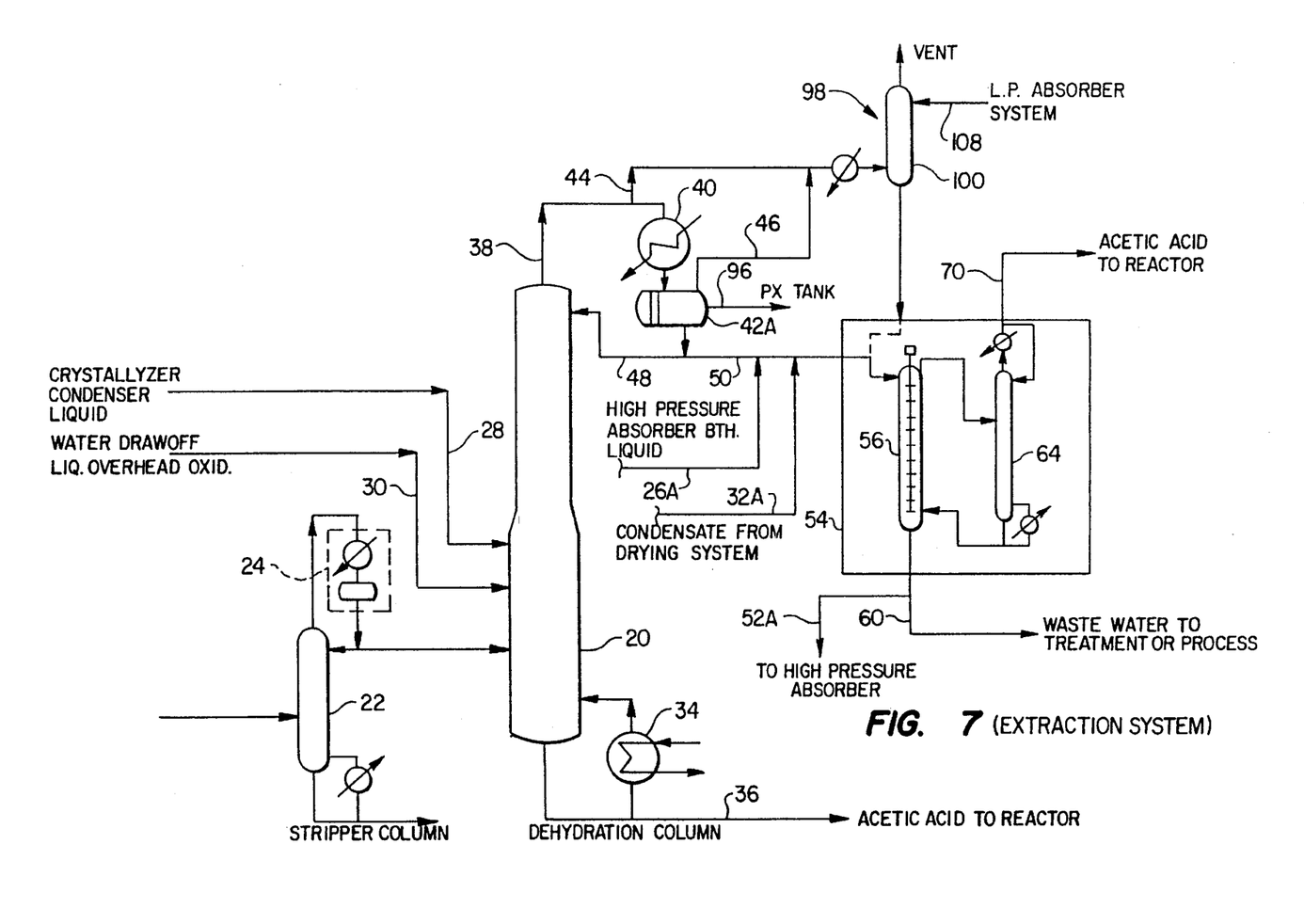
FIG. 7 is a flow diagram of an acetic acid recovery system constructed in accordance with the invention in which the low pressure absorber system of FIG. 5 is employed in a form of the invention as depicted in FIG. 4.

FIG. 7 illustrates a flow sheet for an embodiment of the invention which is much like that of FIG. 6, in that it employs both an extraction system 54 and a low pressure absorption system 98. But it differs from the embodiment of FIG. 6 in that high pressure absorber bottoms liquid is fed directly to the extraction system through line 26A, and condensate from the drying system within the plant is fed to the extraction system 54 through line 32A, thus avoiding the necessity for evaporating the water contained in either of these streams in the dehydration column 20.

Figure 8:
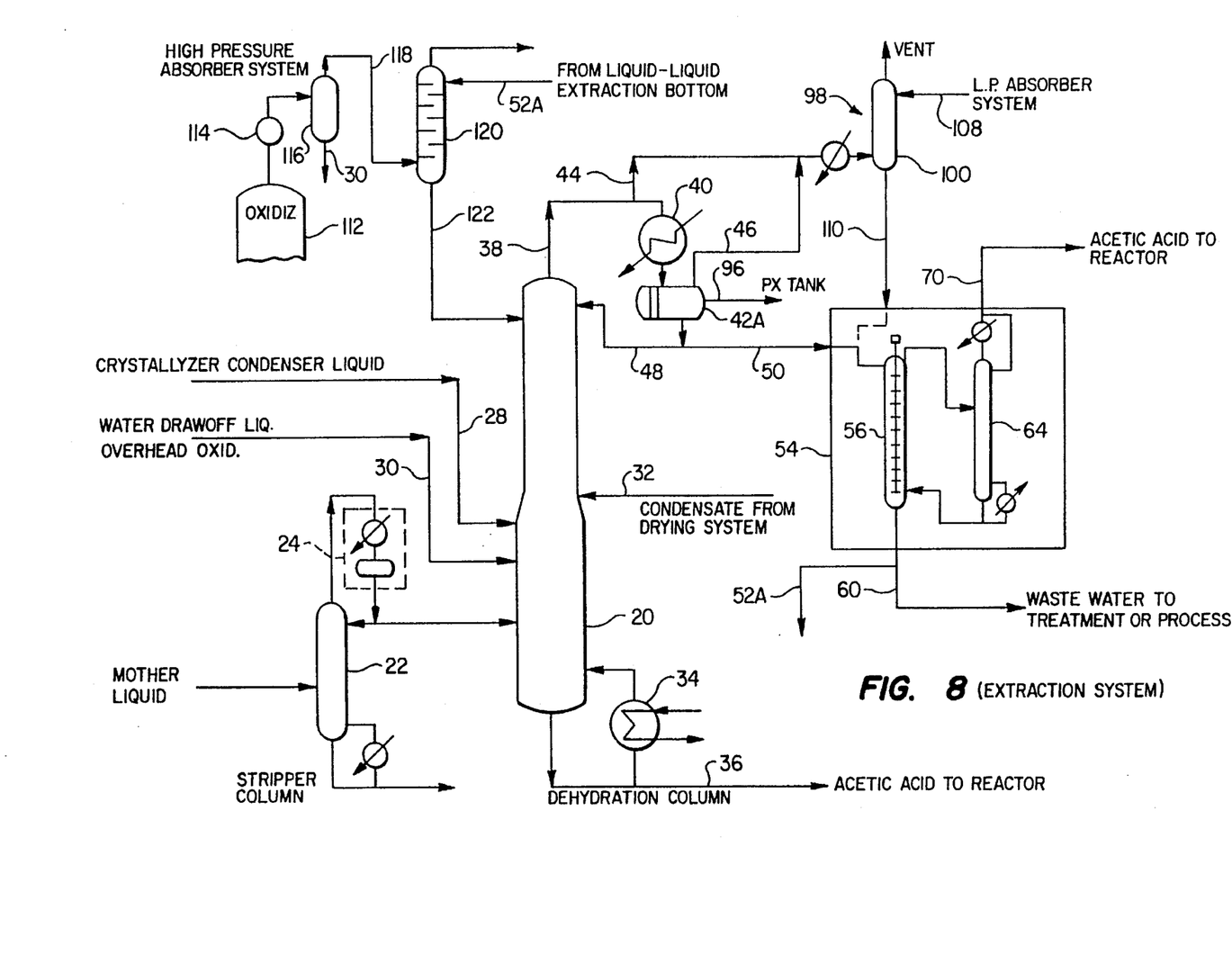
FIG. 8 is a flow diagram of an acetic acid recovery system constructed in accordance with the invention and further including a high pressure absorption system whose bottom output stream is fed to the dehydration column of the system.
Figure 9:
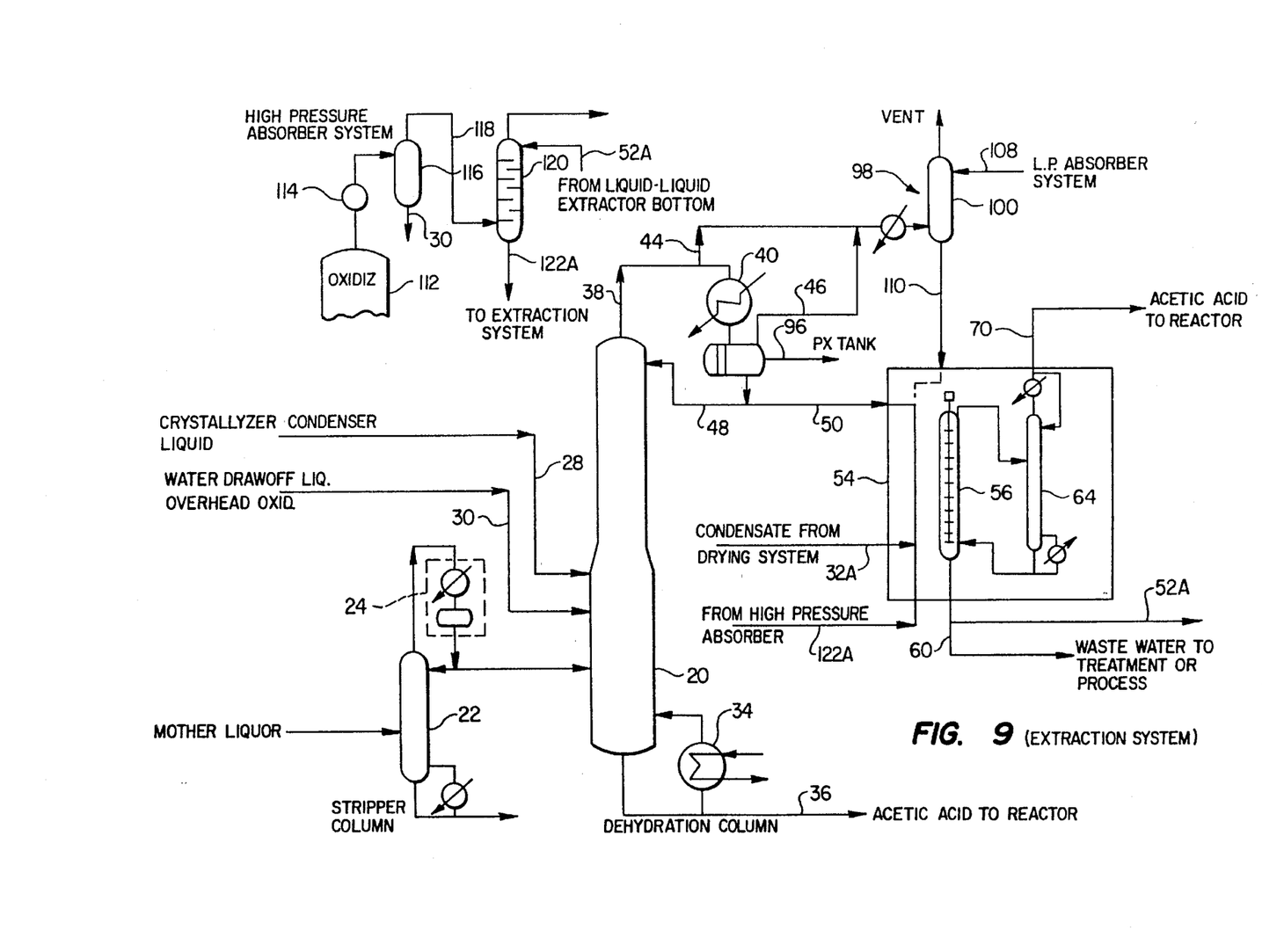
FIG. 9 is a flow diagram of an acetic acid recovery system constructed in accordance with the invention in which the bottom stream from the high pressure absorber system is fed to the extraction system that is provided to process condensate from the overhead stream of the dehydration column.
Figure 10:
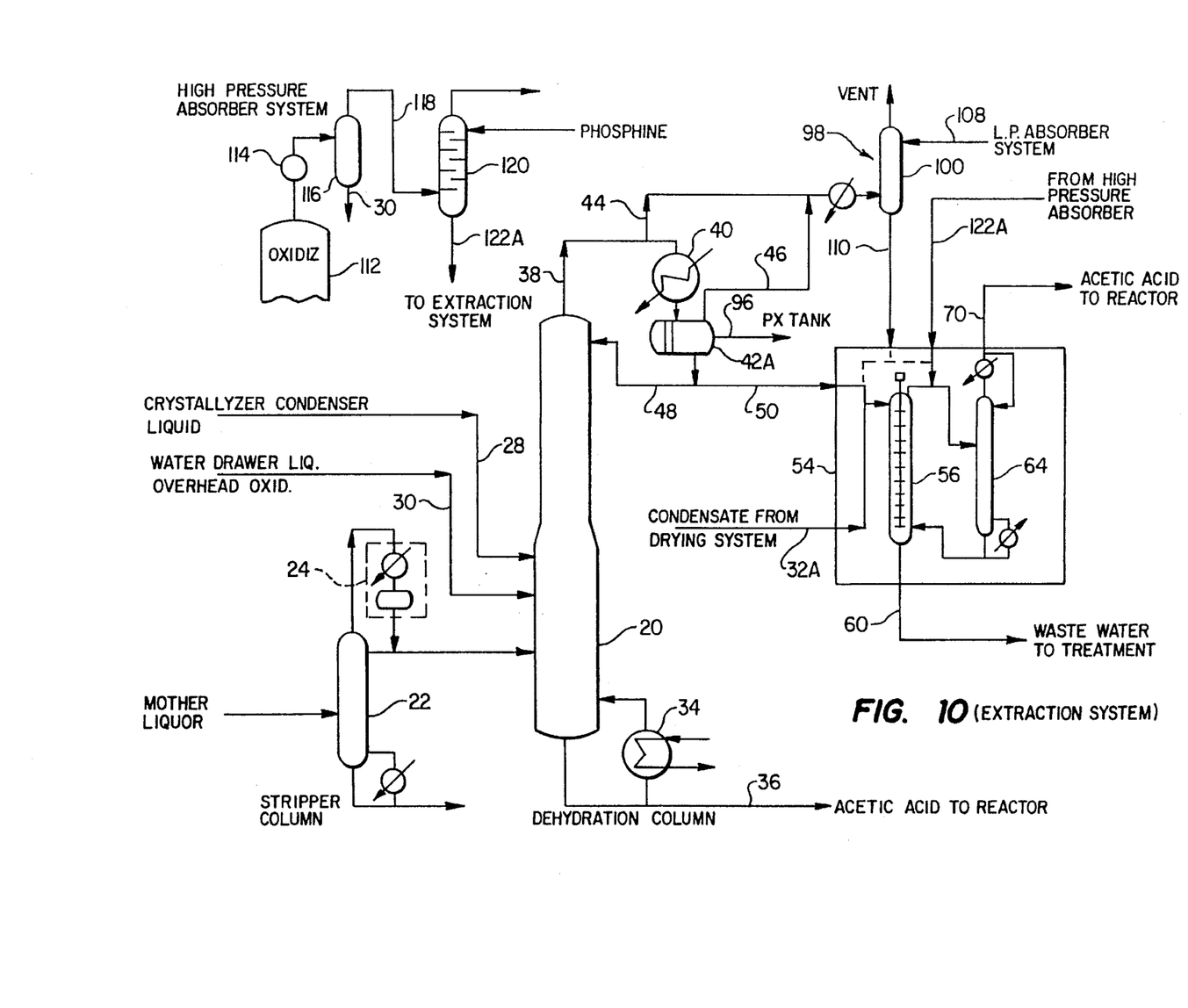
FIG. 10 is a flow diagram of an acetic acid recovery system constructed in accordance with the invention in which the bottom stream from the high pressure absorber system is fed to the extraction system as in FIG. 9, but in which an extractant solvent is used instead of a stream from the dehydration column overhead.

FIGS. 8, 9 and 10 may be considered together. Each shows an embodiment of the invention provided with an extraction system processing condensate from the overhead of the dehydration column designated on each drawing as 54. Each embodiment is also provided with a low pressure absorber system 98, utilizing as inputs streams which, in the prior art system of FIG. 1, are vented to the atmosphere, and which provides an additional stream from its bottom line 110 to the extraction system 54, all in accordance with the invention.

In FIGS. 8, 9 and 10, the oxidizer of the terephthalic acid plant is fragmentarily shown at 112. The overhead stream from the oxidizer is passed through a condenser 114, and into a separator drum 116. The water draw off liquid from the drum 116 passes as a bottom stream 30 to the dehydration column 20. The overhead from the separation drum passes through line 118 into a high pressure absorption column 120. In the case of FIGS. 8 and 9, the solvent for the high pressure absorber system is delivered through line 52A from the largely water bottom stream from extractor 56. In the case of FIG. 8, the bottom stream from the high pressure absorber is passed through line 122 to the dehydration column 20. In the case of FIG. 9, it passes through bottom line 122A to the extraction system 54. In the case of FIG. 10, the same arrangement is used and the bottom stream passes through line 122 directly to the extraction system 54.

FIGS. 9 and 10 differ from one another in that in FIG. 10, a phosphine or other selected extraction solvent or absorption solvent is input through line 124 into the high pressure absorber, instead of relying on condensate from the dehydrator overhead through line 52A as appears in FIG. 9.

From the foregoing, it can be seen that there is considerable flexibility of arrangement of recovery equipment and lines in the acetic acid recovery system of the invention. A guiding principle in taking advantage of such flexibility is the employment of a liquid-liquid extraction system for permitting the presence of a higher concentration in the dehydration column overhead of acetic acid than is tolerable in the prior art, because such extraction system recovers the acetic acid at a low energy cost. The low pressure absorption system provided in accordance with the invention enables the capture of vapor streams that would otherwise be vented to the atmosphere with loss of acetic acid and other organic volatiles, and which creates objectionable atmospheric pollution in many installations. The invention also provides additional flexibility in the handling of the bottom stream from the high pressure absorption system associated with the oxidizer overhead of the terephthalic acid plant, since this may be, but need not be, fed to the dehydration column, but may also be fed to the newly provided extraction system.

We claim:

1. An acetic acid and water separation system in a plant utilizing a water solution of acetic acid comprising:
   (a) a dehydration device having an input line for inputting at least one input acetic acid-containing water stream from said plant and having means to apply heat to said input stream input to said device to separate water from acetic acid in said device to thereby produce an output bottom stream of relatively concentrated acetic acid in water, and an output overhead stream of relatively dilute acetic acid in water;
   (b) condensing means connected to said dehydration device by a dehydration device overhead line to liquefy acetic acid and water from said output overhead stream to form an output overhead condensate;
   (c) a liquid-liquid extraction sub-system connected by a feed line to said condensing means, said sub-system comprising:
      (i) a contactor connected to said condensing means by said feed line for receiving said output overhead condensate and contacting it with a liquid extractant to extract acetic acid from said condensate and thereby form a first contactor output stream containing acetic acid and extractant, and a second contactor output stream containing water; and
      (ii) an extraction sub-system separator device connected by a separator feed line to said contactor to receive said first contactor output stream and separate the acetic acid and the extractant therein to produce an extractant output stream and an acetic acid output stream.

2. An acetic acid and water separation system in accordance with claim 1 in which said liquid extractant boils at a temperature higher than acetic acid, and in which said acetic acid output stream from said extraction sub-system separator device is an overhead stream therefrom.

3. An acetic acid and water separation system in accordance with claim 1 in which said liquid extractant boils at a temperature lower than acetic acid, and in which said acetic acid output stream from said extraction sub-system separator device is a bottoms stream therefrom.

4. An acetic acid and water separation system in a plant utilizing a water solution of acetic acid comprising:
   (a) a dehydration device having an input line for inputting at least one input acetic acid-containing water stream from said plant and having means to apply heat to said input stream input to said device to separate water from acetic acid in said device to thereby produce an output bottom stream of relatively concentrated acetic acid in water, and an output overhead stream of relatively dilute acetic acid in water;
   (b) condensing means connected to said dehydration device by a dehydration device overhead line to liquefy acetic acid and water from said output overhead stream to form an output overhead condensate;
   (c) a liquid-liquid extraction sub-system connected by a feed line to said condensing means, said sub-system comprising:
      (i) a contactor connected to said condensing means by said feed line for receiving said output overhead condensate and contacting it with a liquid extractant to extract acetic acid from said condensate and thereby form a first contactor output stream containing acetic acid and extractant, and a second contactor output stream containing water; and
      (ii) an extraction sub-system separator device connected by a separator feed line to said contactor to receive said first contactor output stream and separate the acetic acid and the extractant therein to produce an extractant output stream and an acetic acid output stream; and
including means for feeding at least one additional relatively dilute acetic acid stream from said plant to said liquid-liquid extraction sub-system along with said output overhead condensate stream from said dehydration device.

5. An acetic acid and water separation system in accordance with claim 4 in which said additional relatively dilute acetic acid stream is a bottoms stream from a high pressure absorber in said plant.

6. An acetic acid and water separation system in accordance with claim 4 in which said additional relatively dilute acetic acid stream is a condensate stream from a drying system.

7. An acetic acid and water separation system in a plant utilizing a water solution of acetic acid comprising:

(a) a dehydration device having an input line for inputting at least one input acetic acid-containing water stream from said plant and having means to apply heat to said input stream input to said device to separate water from acetic acid in said device to thereby produce an output bottom stream of relatively concentrated acetic acid in water, and an output overhead stream of relatively dilute acetic acid in water;

(b) condensing means connected to said dehydration device by a dehydration device overhead line to liquefy acetic acid and water from said output overhead stream to form an output overhead condensate;

(c) a liquid-liquid extraction sub-system connected by a feed line to said condensing means, said sub-system comprising:
   (i) a contactor connected to said condensing means by said feed line for receiving said output overhead condensate and contacting it with a liquid extractant to extract acetic acid from said condensate and thereby form a first contactor output stream containing acetic acid and extractant, and a second contactor output stream containing water; and
   (ii) an extraction sub-system separator device connected by a separator feed line to said contactor to receive said first contactor output stream and separate the acetic acid and the extractant therein to produce an extractant output stream and an acetic acid output stream;

(d) a low pressure absorption unit adapted to contact an absorption solvent and at least one acetic acid containing vapor stream from said acetic acid and water separation system, and a line for feeding absorption solvent after contact with said vapor stream to said liquid-liquid extraction sub-system.

8. An acetic acid and water separation system in accordance with claim 7 in which said acetic acid containing vapor stream is at least a portion of the output overhead stream from said dehydration device.

9. An acetic acid and water separation system in accordance with claim 7 in which said acetic acid containing vapor stream is at least a portion of a vent stream from said condensing means.

10. An acetic acid and water separation system in accordance with claim 7 and further comprising means for delivering to said low pressure absorption unit at least one acetic acid containing vapor stream from a point in said plant other than said acetic acid and water separation system.

11. An acetic acid and water separation system in accordance with claim 7 including means for feeding at least one additional relatively dilute acetic acid stream from said plant to said liquid-liquid extraction sub-system along with said output overhead stream from said dehydration device.

12. An acetic acid and water separation system in accordance with claim 11 in which said additional relatively dilute acetic acid stream is a bottoms stream from a high pressure absorber in said plant.

13. An acetic acid and water separation system in accordance with claim 11 in which said additional relatively dilute acetic acid stream is a condensate stream from a drying system.

14. An acetic acid and water separation system in a plant utilizing a water solution of acetic acid comprising:

(a) a dehydration device having an input line for inputting at least one input acetic acid-containing water stream from said plant and having means to apply heat to said input stream input to said device to separate water from acetic acid in said device to thereby produce an output bottom stream of relatively concentrated acetic acid in water, and an output overhead stream of relatively dilute acetic acid in water;

(b) condensing means connected to said dehydration device by a dehydration device overhead line to liquefy acetic acid and water from said output overhead stream to form an output overhead condensate;

(c) a liquid-liquid extraction sub-system connected by a feed line to said condensing means, said sub-system comprising:
   (i) a contactor connected to said condensing means by said feed line for receiving said output overhead condensate and contacting it with a liquid extractant to extract acetic acid from said condensate and thereby form a first contactor output stream containing acetic acid and extractant, and a second contactor output stream containing water; and
   (ii) an extraction sub-system separator device connected by a separator feed line to said contactor to receive said first contactor output stream and separate the acetic acid and the extractant therein to produce an extractant output stream and an acetic acid output stream;

and further comprising a high pressure absorber sub-system equipped to contact an absorbent liquid at high pressure with a plant overhead vapor stream having acetic acid therein, and means for delivering said absorbent liquid, after contact with said plant overhead vapor stream to said separator sub-system for processing therein.

15. An acetic acid and water separator system in accordance with claim 14 in which said absorbent liquid at high pressure is a largely water stream from said liquid-liquid extraction sub-system contactor.

16. An acetic acid and water separator system in accordance with claim 14 in which said delivering means are connected to deliver said absorbent liquid to said dehydration device.

17. An acetic acid and water separator system in accordance with claim 14 in which said delivering means are connected to deliver said absorbent liquid to the contactor of said liquid-liquid extraction sub-system.

18. An acetic acid and water separator system in accordance with claim 14 in which said delivering means are connected to deliver said absorbent liquid to the extraction sub-system separator device of said liquid-liquid extraction sub-system.

* * * * *